(12) United States Patent
Hancock et al.

(10) Patent No.: US 10,898,172 B2
(45) Date of Patent: Jan. 26, 2021

(54) BIOPSY FORCEPS TOOL

(71) Applicant: CREO MEDICAL LIMITED, Chepstow (GB)

(72) Inventors: Christopher Hancock, Bath (GB); Francis Amoah, Chepstow (GB); Malcolm White, Chepstow (GB); Thomas Craven, Chepstow (GB); Brian Saunders, Rickmansworth (GB); Zacharias P. Tsiamoulos, Harrow (GB)

(73) Assignee: CREO MEDICAL LIMITED, Chepstow (GB)

( * ) Notice: Subject to any disclaimer, the term of this patent is extended or adjusted under 35 U.S.C. 154(b) by 368 days.

(21) Appl. No.: 15/755,925

(22) PCT Filed: Sep. 30, 2016

(86) PCT No.: PCT/EP2016/073493
§ 371 (c)(1),
(2) Date: Feb. 27, 2018

(87) PCT Pub. No.: WO2017/055595
PCT Pub. Date: Apr. 6, 2017

(65) Prior Publication Data
US 2018/0353162 A1 Dec. 13, 2018

(30) Foreign Application Priority Data
Oct. 2, 2015 (GB) .................................. 1517427.9

(51) Int. Cl.
*A61B 10/06* (2006.01)
*A61B 18/18* (2006.01)
(Continued)

(52) U.S. Cl.
CPC .............. *A61B 10/06* (2013.01); *A61B 10/04* (2013.01); *A61B 18/1815* (2013.01);
(Continued)

(58) Field of Classification Search
CPC ..... A61B 10/06; A61B 18/1445; A61B 10/04; A61B 2018/00083; A61B 18/1815;
(Continued)

(56) References Cited

U.S. PATENT DOCUMENTS 5,295,990 A 3/1994 Levin
5,538,008 A * 7/1996 Crowe ................... A61B 10/06
600/564

(Continued)

FOREIGN PATENT DOCUMENTS

CN 201996592 U 10/2011
DE 102006027873 A1 1/2008
(Continued)

OTHER PUBLICATIONS

International Search Report and Written Opinion of related International Patent Application No. PCT/EP2016/073493 dated Mar. 23, 2017.

*Primary Examiner* — Patrick Fernandes
(74) *Attorney, Agent, or Firm* — Arent Fox LLP

(57) ABSTRACT

A biopsy forceps tool (preferably for endoscopic use) in which microwave energy is used to coagulate bleeding after a biological tissue sample is collected between a pair of jaws. The pair of jaws define an enclosure that is isolated from the microwave energy itself and insulated from any thermal changes that occur due to application of the microwave energy. The tool comprises a pair of jaws connected to a coaxial cable, each of the pair of jaws comprising an electrically conductive shell, the jaw assembly being movable between a closed position in which the electrically conductive shells enclose an internal volume for holding a tissue sample and an open position in which the internal volume is exposed in order to receive the tissue sample. The
(Continued)

electrically conductive shells form a Faraday cage around the internal volume when in the closed position.

27 Claims, 5 Drawing Sheets

(51) Int. Cl.
    *A61B 10/04*        (2006.01)
    *A61B 18/00*        (2006.01)
    *A61B 17/00*        (2006.01)
    *A61B 17/29*        (2006.01)

(52) U.S. Cl.
    CPC ............... *A61B 2017/0034* (2013.01); *A61B 2017/2932* (2013.01); *A61B 2018/00101* (2013.01); *A61B 2018/00589* (2013.01); *A61B 2018/00797* (2013.01); *A61B 2018/00821* (2013.01); *A61B 2018/1861* (2013.01); *A61B 2562/182* (2013.01)

(58) Field of Classification Search
    CPC .. A61B 2017/0034; A61B 2018/00101; A61B 2018/0589; A61B 2018/00797; A61B 2018/00821; A61B 2018/1861; A61B 2562/182

See application file for complete search history.

(56) References Cited

U.S. PATENT DOCUMENTS

| | | | |
|---|---|---|---|
| 5,626,607 A * | 5/1997 | Malecki | A61B 17/00234 606/205 |
| 6,585,735 B1 | 7/2003 | Frazier et al. | |
| 2007/0032723 A1* | 2/2007 | Glossop | A61B 5/064 600/424 |
| 2007/0149971 A1* | 6/2007 | Nishimura | A61B 18/1445 606/51 |
| 2011/0237975 A1 | 9/2011 | Secrest et al. | |
| 2012/0101501 A1 | 4/2012 | Nishimura et al. | |
| 2012/0136424 A1* | 5/2012 | Kimura | A61B 18/1445 607/154 |
| 2013/0053835 A1* | 2/2013 | Bacher | A61B 17/29 606/1 |

FOREIGN PATENT DOCUMENTS

| | | |
|---|---|---|
| EP | 2233098 A1 | 3/2010 |
| JP | 1320070 A | 12/1989 |

* cited by examiner

US 10,898,172 B2

BIOPSY FORCEPS TOOL

CROSS-REFERENCE TO RELATED APPLICATIONS

This application is a National Stage Entry of International Patent Application No. PCT/EP2016/073493, filed on Sep. 30, 2016, which claims priority to British Patent Application No. 1517427.9, filed on Oct. 2, 2015. The disclosures of each of the priority applications are incorporated in their entirety herein by reference.

FIELD OF THE INVENTION

The invention relates to a biopsy forceps tool for collected a sample of biological tissue. In particular, he invention relates to an electrosurgical biopsy forceps tool arranged to deliver microwave frequency energy to coagulate or cauterise or seal the remaining tissue after the sample is collected. In particular, the forceps may be used to coagulate a bleeding surface from which the sample is removed (e.g. pulled, cut or resected). The biopsy forceps tool of the invention may be inserted down the instrument channel of an endoscope or a gastroscope, or may be used in laparoscopic surgery or open surgery.

BACKGROUND TO THE INVENTION

Forceps capable of delivering heat energy into grasped biological tissue are known. The heat energy may cauterise the grasped tissue and facilitate coagulation or vessel sealing.

U.S. Pat. No. 6,585,735 describes an endoscopic bipolar forceps in which the jaws of the forceps are arranged to conduct bipolar energy through the tissue held therebetween.

EP 2 233 098 describes microwave forceps for sealing tissue in which the sealing surfaces of the jaws include one or more microwave antennas for radiating microwave frequency energy into tissue grasped between the jaws of the forceps.

Many biopsy procedures are performed using a needle to extract a small cell sample. However, where larger samples are required, it is known to use a biopsy forceps tool to grasp a sample of tissue and separate it from adjoining tissue so that it may be extracted from the patient and tested in vitro. It is common for biopsy forceps to comprise a pair of jaws with sharp cutting edges for removing the sample.

DE 10 2006 027 873 discloses a biopsy forceps tool in which waterjet therapy or radiofrequency (RF) energy is used to selectively remove tissue when grasped by a pair of jaws. This document also suggests using either a low current monopolar electrode or to configure the pair of jaws as bipolar electrodes to perform coagulation.

SUMMARY OF THE INVENTION

At its most general, the present invention provides a biopsy forceps tool (preferably for endoscopic use) in which microwave energy is used to coagulate bleeding after a biological tissue sample is collected between a pair of jaws. The pair of jaws define an enclosure that is isolated from the microwave energy itself and insulated from any thermal changes that occur due to application of the microwave energy.

According to the invention there is provided a biopsy forceps tool comprising: a coaxial cable for conveying microwave energy, the coaxial cable having an inner conductor, an outer conductor and a layer of dielectric material separating the inner conductor from the outer conductor; and a jaw assembly mounted at a distal end of the coaxial cable, the jaw assembly comprising: a pair of jaws, each of the pair of jaws comprising an electrically conductive shell, the jaw assembly being operable to change a relative position of the pair of jaws between a closed position in which the electrically conductive shells engage each other to enclose an internal volume for holding a tissue sample and an open position in which the electrically conductive shells are separated to expose the internal volume in order to receive the tissue sample, wherein the electrically conductive shells form a Faraday cage around the internal volume when in the closed position, and wherein the coaxial cable is connected to deliver microwave energy to the jaw assembly. The microwave energy can be supplied to cause or facilitate coagulation in biological tissue surrounding the outside of the jaw assembly when the pair of jaws are in the closed position. This can assist a clean and safe removal of the tissue sample. The microwave energy can also be supplied when the pair of jaws are in the open position. In this scenario, the pairs of jaws may radiate the microwave energy out from the tool into biological tissue.

The biopsy forceps tool can thus be inserted to a suitable location for treatment (e.g. through an endoscope) while the pair of jaws are in the closed position. Once in position, the pair of jaws may be moved to the open position around a region of tissue to be sampled. During this process no microwave energy may be supplied, i.e. the device may operate "cold". When the region of tissue to be sampled is within the internal volume, the pair of jaws are moved to the closed position, whereby the region of tissue is grasped and then physically separated (i.e. cut or pulled away) from the surrounding tissue. The edges of the pair of jaws may be sharpened, corrugated, serrated or otherwise optimised to facilitate this "cold" cutting procedure. When the pair of jaws reach the closed position, a tissue sample is fully enclosed within the internal volume and a bleeding surface remains outside the tool. To facilitate rapid coagulation of the bleeding surface, microwave energy is delivered to the pair of jaws and sleeve from the coaxial cable (the proximal end of which is connected to a suitable electrosurgical generator. The jaw assembly may be configured to form a transformer structure to match the microwave energy efficiently from the coaxial cable into tissue in contact with the distal end of the jaw assembly. The enclosed tissue sample is protected from the microwave energy because the electrically conductive shells of the pair of jaws form a Faraday cage. In other words, the depth of penetration of the electric field at the frequency of the microwave energy into the internal volume is negligible. For example, at a frequency of 5.8 GHz, the depth of penetration is less than 10 µm.

To protect the enclosed sample from thermal effects during coagulation, each of the pair of jaws may have a thermal insulation layer separating the electrically conductive shell from the internal volume. The thermal insulation layer may be made from a plastic (e.g. PEEK, nylon, Teflon), ceramic or even a metal with low thermal conductivity. A low thermally conducting plastic is preferred. In an embodiment, the pair of jaws may be formed from a single piece of material (e.g. moulded plastic) having a layer of metallisation provided over its outer surface. In this example, the pivotability between the pair of jaws may be provided by the intrinsic flexibility of the piece of material or by a living hinge or the like.

Preferably the thickness of the electrically conducting shell is five or more skin depths deep at the frequency of the microwave energy. This means that the electric field will be reduced to 1% of its value at the surface of the jaws and the power that could possibly cause heating within the internal volume would be less than 0.5% of the value at the surface. For example, if the frequency of microwave energy is 5.8 GHz and silver is used as the material for the electrically conductive shells, the skin depth is 0.83 µm, so the thickness of the electrically conductive shell is preferably greater than 4 µm.

The electrically conducting shells engage each other along opposing peripheral edges when the pair of jaws are in the closed position. For example, each of the electrically conductive shells may resemble an upturned bowl or trough, the rim of which forms the peripheral edge. The opposing peripheral edges may be sharpened or may have a serrated or saw-tooth profile. A sharply undulating profile may assist in preventing microwave field from penetrating into the internal volume. The opposing peripheral edges may overlap when the pair of jaws are in the closed position. For example, one of the opposing peripheral edges may include a recessed groove that is arranged to receive the other peripheral edge.

The pair of jaws may be pivotably connected to each other. Herein, the phrase "pivotably connected" may mean that one or both jaws are rotatably movable relative to the other jaw about a pivot axis to increase or decrease an angle between the jaws.

In an embodiment, the pair of jaws may be pivotable about a hinge at their proximal ends. The pair of jaws may be biased towards the open position, e.g. by providing a spring in the hinge. This arrangement may enable the opening of the pair of jaws to occur automatically through the removal of a radial constraint on the pair of jaws. For example, a sleeve may be arranged to surround the pair of jaws when they are in the closed position. The radial constraint may be provided by the sleeve. The removal of the radial constraint may be effected by relative axial movement between the sleeve and the pair of jaws.

For example, the sleeve may be axially slidable relative to the pair of jaws between a forward position in which the sleeve covers the pair of jaws and a retracted position in which the pair of jaws protrude outwardly from the sleeve. Thus, when the sleeve is in the forward position the pair of jaws can be constrained to occupy the closed position and when the sleeve is slid into the retracted position the pair of jaws are able to adopt the open position.

In another example, the pair of jaws may be axially slidable relative to the sleeve between a retracted position in which the sleeve covers the pair of jaws and an extended position in which the pair of jaws protrude from the sleeve. Thus, when the pair of jaws are in the retracted position they are constrained to occupy the closed position and when the pair of jaws is slid into the extended position they are able to adopt the open position.

The coaxial cable may have a terminal connector at its distal end, the terminal connector having an axially extending conductive pin electrically connected to the inner conductor of the coaxial cable. The jaw assembly may include a conductive tube slidably engaged with the conductive pin, the conductive tube being electrically connected to the electrically conductive shells of the pair of jaws. The pair of jaws may be moved axially by axial movement of the conductive tube.

Axial movement of either the sleeve or the conductive tube may be effected by a control rod (e.g. a push rod) that is movable axially relative to the coaxial cable. For example, the control rod may be connected to the conductive tube, whereby the conductive tube is slidable relative to the conductive pin by movement of the control rod relative to the coaxial cable. Alternatively, the control rod may be connected to the sleeve, whereby the sleeve is movable axially relative to the pair of jaws by movement of the control rod relative to the coaxial cable.

The control rod may extend alongside the coaxial cable. Alternatively, the inner conductor of the coaxial cable may be hollow, and the control rod may be slidably disposed in the hollow inner conductor.

The sleeve may comprise an inner dielectric layer and an outer conductive layer that is electrically connected to the outer conductor of the coaxial cable. Alternatively, the sleeve may be insulated from the coaxial cable but may comprise a proximal choke to inhibit the formation of unwanted microwave fields. The electrically conductive shells may be electrically connected to the inner conductor of the coaxial cable. This arrangement transfers the microwave energy to the jaw assembly.

The inner dielectric layer of the sleeve may both abut (i.e. physically contact) and electrically insulate the outer conductive layer of the sleeve from the electrically conductive shells of the pair of jaws.

In both examples described above, the speed of opening of the pair of jaws may be controlled by shaping the outer profile of the electrically conductive shells that engage the distal end of the sleeve.

In an embodiment, the control rod may act more directly to change the relative position of the pair of jaws. For example, the control rod may be movable axially relative to the coaxial cable, and the jaw assembly may include a cam mechanism engaged with the control rod to transform axial movement of the control rod into pivoting relative movement between the pair of jaws.

In an embodiment, the control rod may be rotatable, and the jaw assembly may include a rotary joint in engagement with the control rod to transform rotating movement of the control rod into pivoting relative movement between the pair of jaws.

The tool may have a protective feed cable surrounding the coaxial cable and jaw assembly. The sleeve may be a distal portion of the protective feed cable.

A temperature sensor may be mounted in the internal volume, e.g. to monitor the effect of coagulation on the temperature of the enclosed sample. It may also be desirable to mount one or more temperature sensors on an outer surface of the jaw assembly to monitor the tissue temperature in order to ensure coagulation has successfully been achieved. The temperature sensors may be thermocouples.

Herein, "microwave energy" may be used broadly to indicate a electromagnetic energy in a frequency range of 400 MHz to 100 GHz, but preferably in a range of 1 GHz to 60 GHz, more preferably 2.45 GHz to 30 GHz or 5 GHz to 30 GHz. The invention may be used at a single specific frequency, such as any one or more of: 915 MHz, 2.45 GHz, 3.3 GHz, 5.8 GHz, 10 GHz, 14.5 GHz and 24 GHz.

The biopsy forceps of the invention may be configured for insertion down an instrument channel of an endoscope, or may be arranged for use in laparoscopic surgery or in a NOTES procedure or in a general open procedure. The diameter of the instrument channel in the endoscope may be 1.5 mm, 1.6 mm, 1.8 mm, 2.2 mm, 2.8 mm or 3.2 mm, but is not limited to these values.

The biopsy forceps of the invention may be used to collect tissue samples in any region of the body, e.g. colon, oesophagus, lungs, liver, kidney, prostate, etc.

When the jaws are closed, the device may also be used as a general purpose haemostat to stem bleeding vessels or to pre-coagulate vessels to prevent them bleeding when tissue resection or cutting is performed using another device.

BRIEF DESCRIPTION OF THE DRAWINGS

Embodiments of the invention are described in detail below with reference to the accompanying drawings, in which.

DETAILED DESCRIPTION; FURTHER OPTIONS AND PREFERENCES

Figure 1:
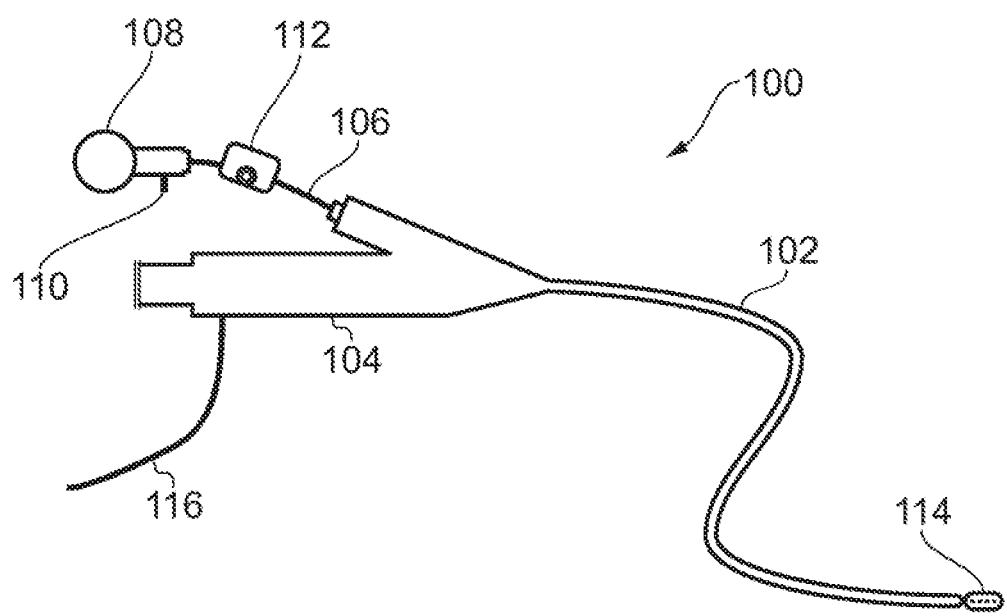
FIG. 1 is a schematic drawing of an endoscopic biopsy forceps tool that is an embodiment of the invention.

FIG. 1 shows a schematic view of an endoscopic biopsy forceps tool 100 that is an embodiment of the invention. In this embodiment, a biopsy forceps tool such as those discussed below is inserted through the instrument channel 102 of an endoscope 104. As discussed below, the biopsy forceps tool can comprise a long flexible feed cable that passes through the instrument channel and terminates at a distal jaw assembly 114 for collecting a biological tissue sample. The proximal end of the feed cable 106 terminates at a handle 108, which includes a pull trigger 110 for operating the distal jaw assembly (discussed below in more detail). A hand grip 112 may be clamped onto the feed cable to provide a means of rotating the cable, and therefore controlling the orientation of the distal jaw assembly 114. The pull trigger maybe a slider or a thumb wheel or a rotating knob.

The feed cable may comprise an outer sleeve that contains a coaxial cable for conveying microwave energy to the distal jaw assembly and a push rod for mechanically actuating the distal jaw assembly. Microwave power may be supplied to the endoscope 104 (in particular to the coaxial cable carried by the feed cable) via a power supply line 116 from a separate microwave generator (not shown).

The outer sleeve of the feed cable may include internal braids which provide torque stability, i.e. resist twisting of the sleeve relative to the coaxial cable. Ideally, the translation between rotation of the handle at the proximal end of the device and the circular movement of the jaws at the distal end will be 1:1, but lesser translation ratios, e.g. 1:2 may be sufficient.

Figure 2A:
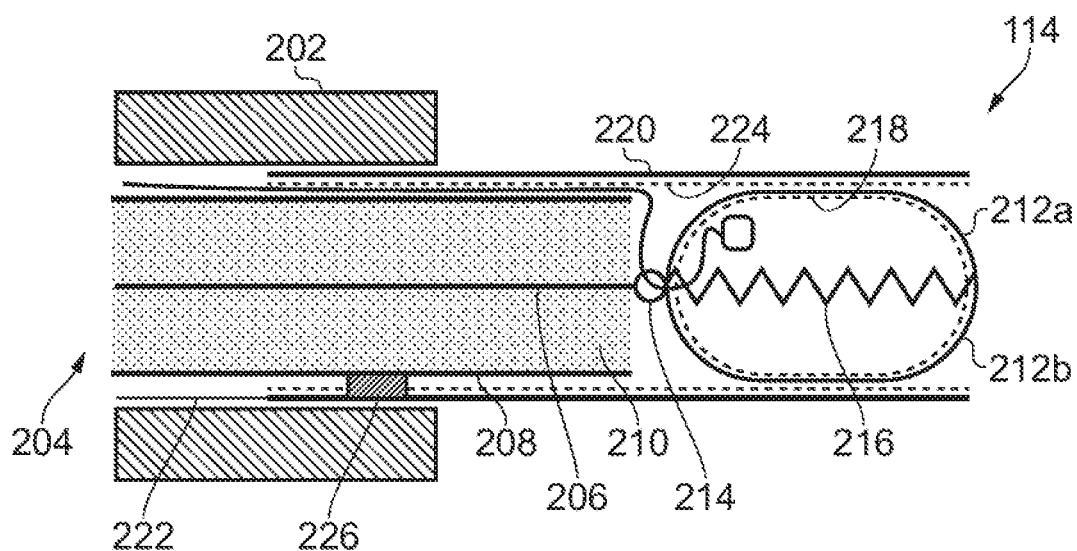
FIG. 2A is a schematic cross-sectional view through the distal end of a biopsy forceps tool that is an embodiment of the invention in a closed configuration.

FIG. 2A shows a schematic representation of a cross-sectional view of the distal jaw assembly 114 according to a first embodiment when in a closed configuration. As mentioned above, the distal jaw assembly 114 protrudes from a distal end of the feed cable 202. A coaxial cable 204 conveyed by the feed cable 202 comprises an inner conductor 206, an outer conductor 208 and a dielectric material 210 separating the inner conductor 206 from the outer conductor 208. At the distal end of the coaxial cable 204, a pair of jaws 212a, 212b is disposed. The pair of jaws 212a, 212b are pivotably connected to each other, e.g. by a hinge 214 at the proximal end of the pair of jaws 212a, 212b. The pair of jaws 212a, 212b form a shell that encloses a volume for collecting a sample of biological tissue. In this embodiment, the shell resembles a lozenge, but in practice there is not limitation to the shape of the shell. The pivotable functionality of the pair of jaws acts to enable the jaws to move apart to form an entrance to the volume that faces towards the distal end of the jaw assembly (see FIG. 2B). Each of the pair of jaws 212a, 212b comprises an electrically conductive outer shell (e.g. made of metal, such as copper, silver, gold or aluminium). In one example, the electrically conductive outer shell is formed from stainless steel with an silver or gold plating on its outer surface. The inner stainless steel layer has a lower thermal conductivity than the outer plating, which improves the thermal barrier between the internal volume and the outer surface to ensure that the tissue sample does not become damaged due to being heated. In the embodiment illustrated in FIG. 2A, each of the pair of jaws 212a, 212b comprises a thin layer of thermal insulation 218. This layer may be made from a material having a low thermal conductivity. For example, a plastic material such as polystyrene may be used. The layer of thermal insulation 218 may be formed (e.g. bonded or otherwise secured) to an inner surface of the corresponding electrically conductive outer shell. Alternatively, the layer of thermal insulation may be moulded first and have a layer of metallisation or plating formed thereon to provide the electrically conductive shell. In this embodiment, each of the pair of jaws 212a, 212b form open cup-like structures which oppose one another at their open edges. The opposing edges 216 of the pair of jaws 212a, 212b may have a serrated or saw-tooth profile. The opposing edges 216 are arranged to mate (i.e. fit together) when the jaw assembly is in the closed configuration. There may be a groove along the edges to ensure that fields are present inside the jaws, i.e. this would form an EM gasket or seal to prevent microwave fields entering the tissue contained therein, which may lead to tissue heating. The electrically conductive outer shells are electrically connected in the closed configuration. This means that the shell of conductive material may act as a Faraday cage to prevent or inhibit electric fields (specifically a microwave field from the energy supplied from the coaxial cable) from existing within the enclosed volume when the distal jaw assembly is closed.

In order to prevent electric fields from penetrating through the electrically conductive outer shell of the pair of jaws 212a, 212b, the electrically conductive material that forms these shells has a thickness of at least three skin depths of the material at the frequency of the microwave energy that is conveyed by the coaxial cable, ideally, this will be five skin depths or more.

The electrically conductive outer shells of the pair of jaws 212a, 212b are electrically connected to the inner conductor 206 of the coaxial cable 204, e.g. via a connection that extends through the hinge 214.

The distal jaw assembly 114 further comprises a sliding sleeve 220 which is movable axially with respect to the coaxial cable 204 to change the distal jaw assembly 114 between closed and open configurations. The sliding sleeve 220 is mounted around the coaxial cable 204 and within the feed cable 202. In an alternative embodiment, the sleeve may be part of the feed cable itself, i.e. the feed cable may be retractable with respect to the coaxial cable within it. A proximal end of the sliding sleeve is connected to a push rod 222, which extends proximally through the feed cable 202 and is controllable by the pull trigger 110 discussed above.

The outer sleeve 220 comprises an outer electrically conductive layer and an inner dielectric layer 224. The inner dielectric layer 224 abuts the outer surface of the pair of jaws 212a, 212b and electrically insulates them from the outer electrically conductive layer. The outer electrically conductive layer is electrically connected to the outer conductor 208 of the coaxial cable 204 by a connecting portion 226 that extends through the inner dielectric layer 224 in a region spatially separated from the pair of jaws 212a, 212b.

In this embodiment, the pair of jaws 212a, 212b are biased away from each other, e.g. by including a spring in the hinge 214, so that they are urged against the sliding sleeve 220. Thus, when the sliding sleeve is slid in a proximal direction relative to the pair of jaws 212a, 212b (to the left in FIG. 2A), the pair of jaws 212a, 212b protrudes from the sleeve and opens to provide access to the enclosed volume under the effect of the biasing force. The nature of the movement is controlled by providing a suitable outer profile to the outer shells of the pair of jaws 212a, 212b.

Figure 2B:
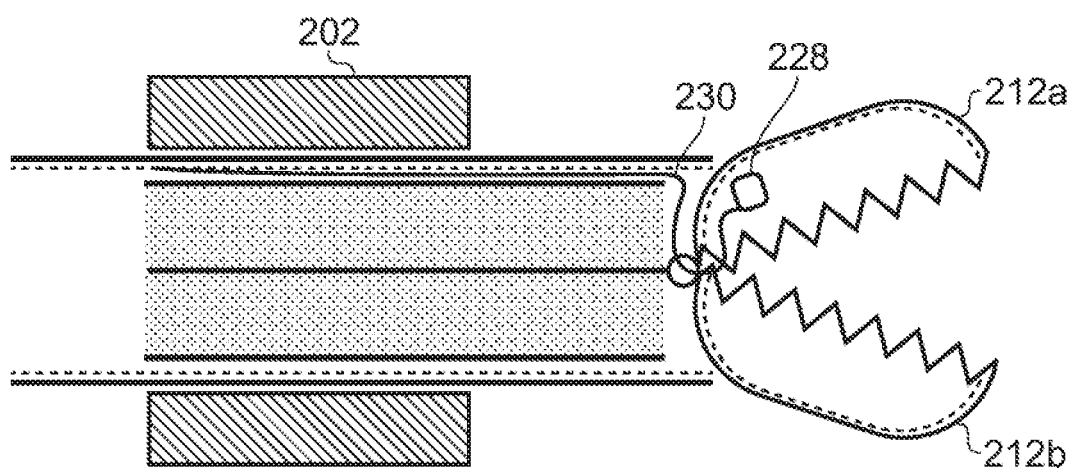
FIG. 2B is a schematic cross-sectional view through the distal end of the biopsy forceps tool of FIG. 2A in an open configuration.

FIG. 2B shows a schematic representation of the distal jaw assembly shown in FIG. 2A when in an open configuration, i.e. when the sleeve 220 has been slid proximally to expose the pair of jaws 212a, 212b. The pair of jaws 212a, 212b are thus open to receive a sample of biological tissue.

In use, the device is inserted into a treatment (sample extraction) location while in the closed configuration. Once in position, the sleeve 220 may be retracted to open the pair of jaws 212a, 212b. When the open jaws are position against a desired portion of tissue, the sleeve 220 is pushed distally over the jaws, which thus grasp and remove a sample of the biological tissue. The opposing edges of the pair of jaws 212a, 212b may be sharpened to improve the effectiveness of the cut. Once the tissue sample is removed and enclosed within the shell of the jaws, microwave energy is supplied through the coaxial cable to coagulate the bleeding surface that remains after the sample is removed. The microwave field emitted by the outer conductive layer of the sleeve and the pair of jaws is discussed in more detail below. Since the closed jaws act as a Faraday cage and the depth of penetration of the microwave field is negligible compared with the thickness of the shell, the sample is protected from the microwave field and therefore unwanted tissue effects are avoided.

A temperature sensor 228 (e.g. a miniature thermocouple or the like) may be mounted inside the enclosed volume to monitor the temperature of the tissue sample. The temperature sensor 228 may be connected to an external processor by a wire 230, which may run through the hinge 214 and along the inside of the feed cable. Temperature sensors may also be connected to the outer jaws or the shell to measure the temperature of the tissue when microwave coagulation is required.

Figure 3A:
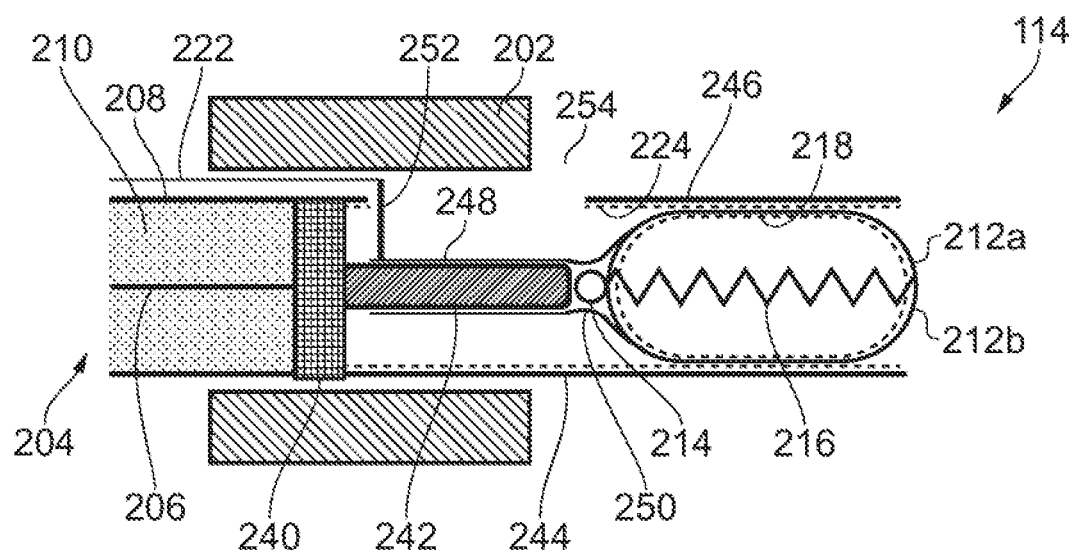
FIG. 3A is a schematic cross-sectional view through the distal end of a biopsy forceps tool that is another embodiment of the invention in a closed configuration.

FIG. 3A shows a schematic representation of a cross-sectional view of the distal jaw assembly 114 according to a second embodiment when in a closed configuration. Components that are configured in the same way as the distal jaw assembly shown in FIGS. 2A and 2B are given the same reference numbers and are not described again.

Figure 3B:
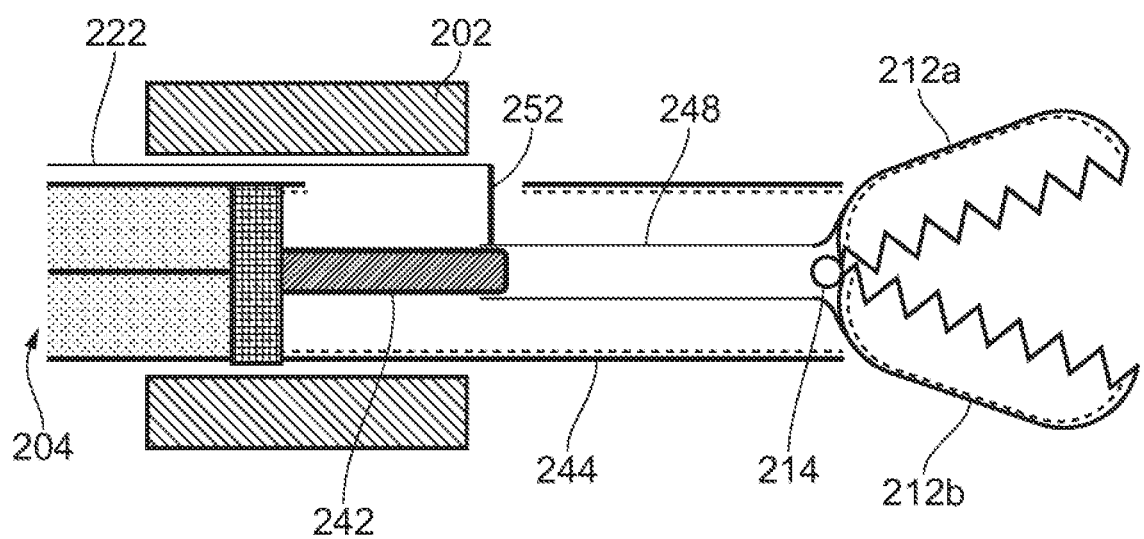
FIG. 3B is a schematic cross-sectional view through the distal end of the biopsy forceps tool of FIG. 3A in an open configuration.

The embodiment shown in FIGS. 3A and 3B differs from the embodiment of FIGS. 2A and 2B in that the pair of jaws 212a, 212b are connected to the push rod 222 and are axially slidable relative to the coaxial cable 204 to move the assembly between the closed and open configurations.

In this embodiment, the coaxial cable 204 terminates at its distal end with a connector 240. The connector 240 has a distally extending central conductor 242, which is electrically connected to the inner conductor 206 of the coaxial cable 204. A guide sleeve 244 is attached to the connector 240 and extends distally away therefrom to form a channel through which the pair of jaws 212a, 212b are slidable. The guide sleeve 244 is configured in a similar way to movable sleeve 220 discussed above, in that it has an electrically conductive outer layer 246 and a dielectric inner layer 224 which insulates the electrically conductive outer layer 246 from the electrically conductive outer shell of the pair of jaws 212a, 212b.

A conductive tube 248 is slidably mounted on the central conductor 242 of the connector 240. The conductive tube 248 is electrically connected to the central conductor 242, e.g. through physical contact, whereby in combination these components are axially extendable in a telescopic or trombone-like manner. The conductive tube 248 in turn is electrically connected to the outer conductive shells of the pair of jaws 212a, 212b, e.g. using a piece of foil 250 or other flexible conductor. Both these electrical connection may be designed, e.g. using simulations or the like, to ensure integrity in terms of impedance in order to limit or minimise mismatch. It is desirable to have a good impedance match between the connected sections to ensure that maximum power is delivered into the tissue load. Alternatively, the distances involved are such that the electrical phase change over the physical length is negligible. This connection could be made using two slidable tubes, a flexible substrate, e.g. Rflex 8080 from Rogers Corporation, or by use of a rotatable co-axial joint. The conductive tube 248 is physically connected to and movable with the push rod 222, e.g. via a rigid support strut 252. A slot-like aperture 254 is formed in the guide sleeve 244 to enable the support strut 252 to connect with the push rod outside the sleeve. In other embodiments, the guide sleeve may be formed by the inner surface of the feed cable 202, in which case the aperture may not be necessary.

FIG. 3A shows the pair of jaws 212a, 212b fully retracted within the guide sleeve 244. This is configuration adopted by the distal jaw assembly 114 after a sample has been collected and when it may be desirable to apply microwave energy through the coaxial cable to generate a coagulating effect at the distal end of the instrument.

FIG. 3B shows the pair of jaws 212a, 212b extended out of the guide sleeve 244 by sliding the conductive tube 248, which may have a wall thickness of around five skin depths (which is around 5 µm at 5.8 GHz) along the central conductor 242. The pair of jaws 212a, 212b included a hinge 214 that is biased to urge the jaws apart. In this open configuration, the pairs of jaws can grasp a portion of biological tissue to be collected and retained in the volume enclosed by the jaws when in the closed configuration. It maybe preferable for microwave energy not to be delivered when the jaws are in the open configuration in order to avoid unwanted thermal damage to the tissue sample.

The instrument described above may combine the functions of a biopsy probe and a coagulation/ablation tool that can be used to obtain a biopsy sample and also seal the sample hole and prevent live torn tissue from being spread by or after the biopsy; this is of particular importance when the tissue to be removed is cancerous. Many biopsy tools have a small tool of about 2 mm diameter, with two jaws that can be closed to excise a small sample a few millimetres across. The discussion above demonstrates how similar jaws can be energised using microwave power so that they might be used as part of a coagulation/ablation tool to treat the biopsy site immediately after the sample is taken, without introducing a separate tool. The device may also be used as a standalone haemostat.

In order for such a tool to be useful it is desirable that:
- the sample does not get too hot, either through direct heating by microwaves or by conduction from the tissue to be coagulated/ablated.
- microwave energy is transmitted in a controlled manner from a suitable part of the tool into a desired target tissue.
- the tool is designed to have low insertion loss and high return loss, so that a large proportion of the supplied microwave energy is applied to the desired tissue without the supply cable or tool getting too hot.

As explained above, it is possible eliminate or substantially reduce direct heating of the sample by configuring the pair of jaws so that they form a Faraday cage when closed and making the jaws from an insulating material with a layer of metallisation that is several skin depths thick or by making the jaws from metal only, which will also keep the sample cool due to the limited depth of penetration of the electromagnetic field. A Faraday cage exists when a volume is enclosed by a hollow electrically conducting shell. The hollow conducting shell is the Faraday cage. Where there is a Faraday Cage, the electric fields inside the cage are either zero, or, in reality, much smaller than those outside the cage. A Faraday cage will exclude microwave fields from its enclosed volume and prevent direct microwave heating of any sample in that volume.

In order to achieve this in practice, there needs to be a conducting shell over large parts of the biopsy tool, to form a conducting cage around the sample when the jaws are closed. It is necessary for the parts of this shell to be electrically connected together, and to be thick enough so that the electric currents do not penetrate from one side of the shell to the other. To prevent currents penetrating from one side of the shell to the other the shell needs to be typically at least 3 skin depths thick, where the skin depth is determined by the electrical and magnetic properties of the material, and the microwave frequency, as $$\delta = \sqrt{\frac{\rho}{\pi f \mu}},$$

where $\delta$ is the skin depth (in m), f is the frequency (in Hz), $\rho$ is the resistivity of the conductor (in $\Omega \cdot m$), and $\mu$ is the (magnetic) permeability of the conductor (in $Hm^{-1}$). The skin depths for copper, silver, gold and aluminium are close to 1 micron for 5.8 GHz, and for iron and steel are about one tenth of this, so the conducting shell does not need to be very thick. Also, the shell does not need to be an unbroken layer of conductor, but may have holes in it, if these are substantially less than a wavelength across the largest dimension. At 5.8 GHz holes less than 0.5 mm across can be ignored.

If there are two jaws, each of which has a conductive outer coating, and they touch at the back where the hinge is, but do not touch anywhere else along the edge of the jaws between the two halves, then it is in theory possible for microwave radiation to penetrate between the jaws. For this to happen there would need to be a strong microwave electric field perpendicular to the gap between the jaws. If the microwave signal is introduced from the back of the jaws, where they are connected, the symmetry of the jaw construction means that such a signal is not generated in the feed or tool. However, such a signal could be generated by reflection from the tissue to be coagulated/ablated, if contact with tissue was only made with one side of the jaws. To prevent this from happening, it is desirable to incorporate teeth or prongs at the front of the jaws, which made good conducting contact when the jaws were closed. This would strongly reduce the effect of the load being asymmetrical.

In order to reduce the effect of heating the tissue sample by conduction from the surrounding tissue, it is desirable for the biopsy jaws to incorporate a thermal insulating layer. Alternatively or additionally, the heat capacity of the jaws can be increased by providing a thermal path from the jaws to a heat sink with a bigger heat capacity. For example, the coaxial cable may act as a heat sink.

The conduction heating of the sample inside the biopsy tool can be estimated, although it may be preferably to incorporate a small sensor within the jaws to enable actual measurements to be taken. Such measurement may allow the power input to be accurately related to temperature rise in the biopsy sample due to heat conduction from the surrounding tissue.

The coaxial cable used to feed the microwave power to the distal jaw assembly may have a typical impedance of 50 ohms. The section of transmission line where the microwave power is fed around the jaws has a lower impedance than this. The match to tissue at the end of this section can be improved by optimising the length of this section.

Figure 4:
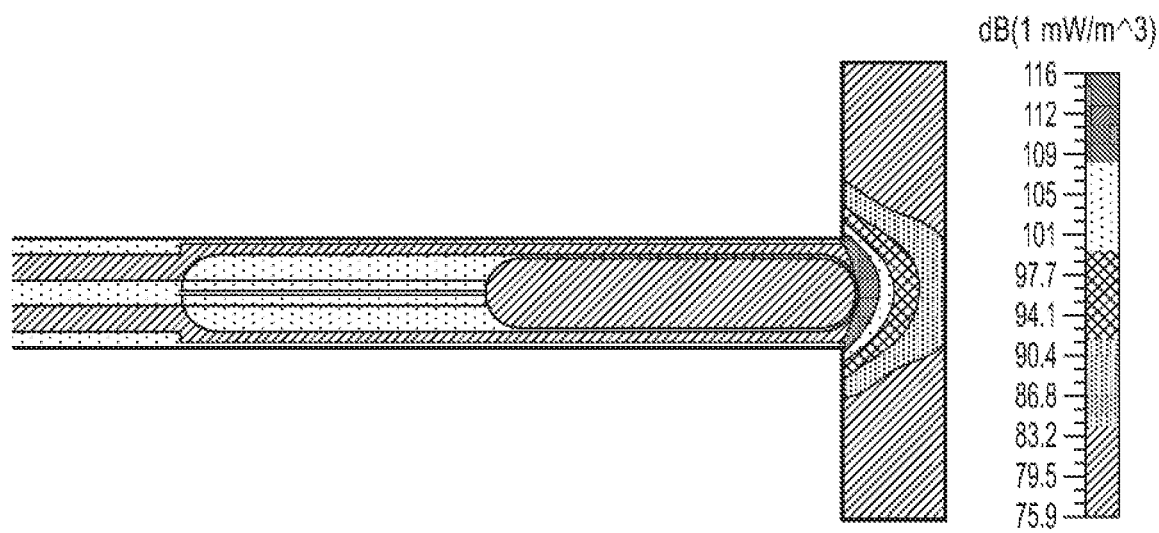
FIG. 4 is a side view of a modelled biopsy forceps tool showing simulated power loss density in blood.

FIG. 4 shows a simulation of a distal jaw assembly according to the invention. The distal jaw assembly may be treated as a transformer, which is formed between the outer conducting layer of the pair of jaws and the conducting layer of the outer sleeve (which in this example is slidable over the pair of jaws). The conducting layer of the outer sleeve must make electrical contact with the outer conductor of the coaxial cable, unless it continues for long enough (e.g. about 7 mm) to form a quarter-wave choke. In that case the whole inside of the sleeve may be lined with a thin insulating layer, e.g. PTFE. In this simulation, the low impedance section around the biopsy jaws is 14.7 mm long and the frequency of the microwave energy 5.8 GHz. The match to tissue in this case is very good. 14.7 mm is close to a half wavelength in this transmission line. This implies that the impedance presented by the tissue at the end of the biopsy probe is close to 50 ohms, as a transformer close to a half-wave has a transformer ratio close to 1.

Figure 5:
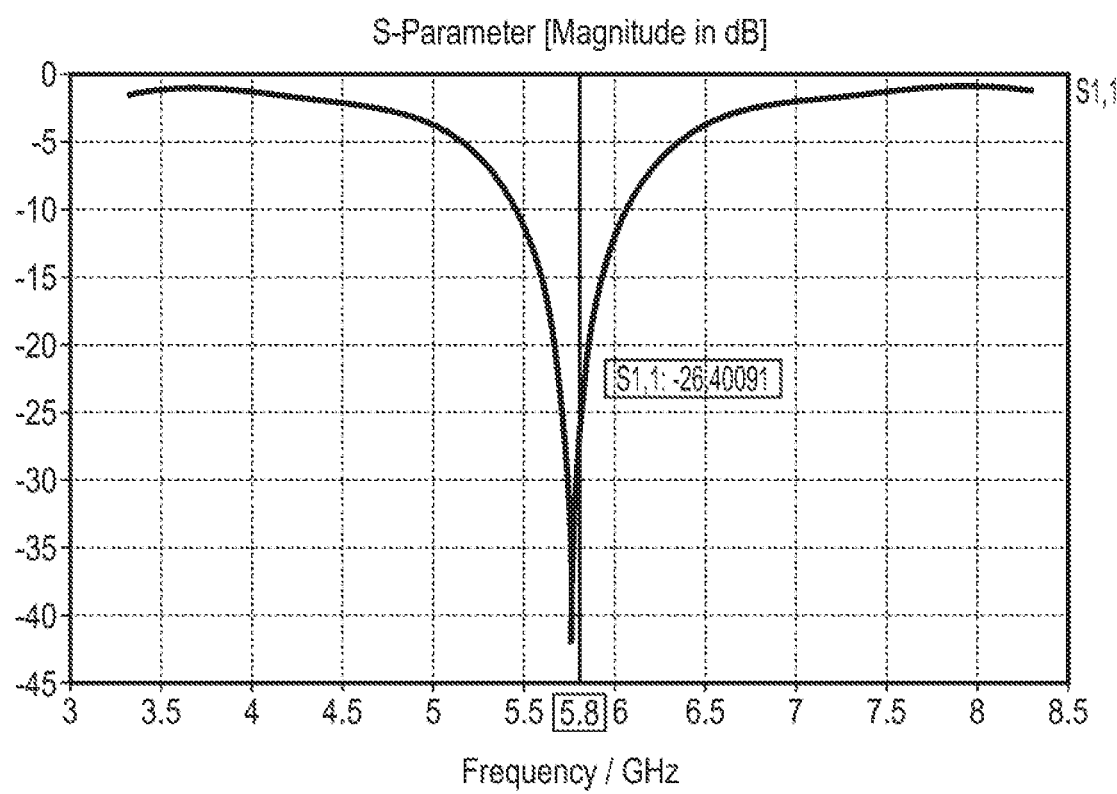
FIG. 5 is a graph showing return loss for the modelled biopsy forceps tool shown in FIG. 4.

In FIG. 4, the maximum power density is 116 dBm/m$^3$, which translates to $(10^{11.6} \times 10^{-3})/10^9$ W/mm$^3$=0.398 W/mm$^3$. The average specific heat capacity of blood is 3617 J/kg·K (range 3300 J/kg·K to 3900 J/kg·K) and the average density of blood is 1050 kg/m$^3$ (range 1025 kg/m$^3$ to 1060 kg/m$^3$). Therefore, the average specific heat capacity of blood is around 3.6 mJ/mg·K, and that the density of tissue is about 1.05 mg/mm$^3$ so that the volumetric heat capacity of the tissue is about 3.6 mJ/mg·K×1.05 mg/mm$^3$=3.78×10$^{-3}$ J/K·mm$^3$. Using a source of 0.398 W/mm$^3$ therefore provides a rate of tissue heating of 0.398-3.78×10$^{-3}$=105 Ks$^{-1}$ 1 mm$^3$ of blood. FIG. 5 shows the return loss of the arrangement in FIG. 4. This good result indicates that a useable return loss should be achievable for a number of conditions and that there should be some scope for modifying the precise shape of the pair of jaws without affecting the power delivery.

Figure 6:
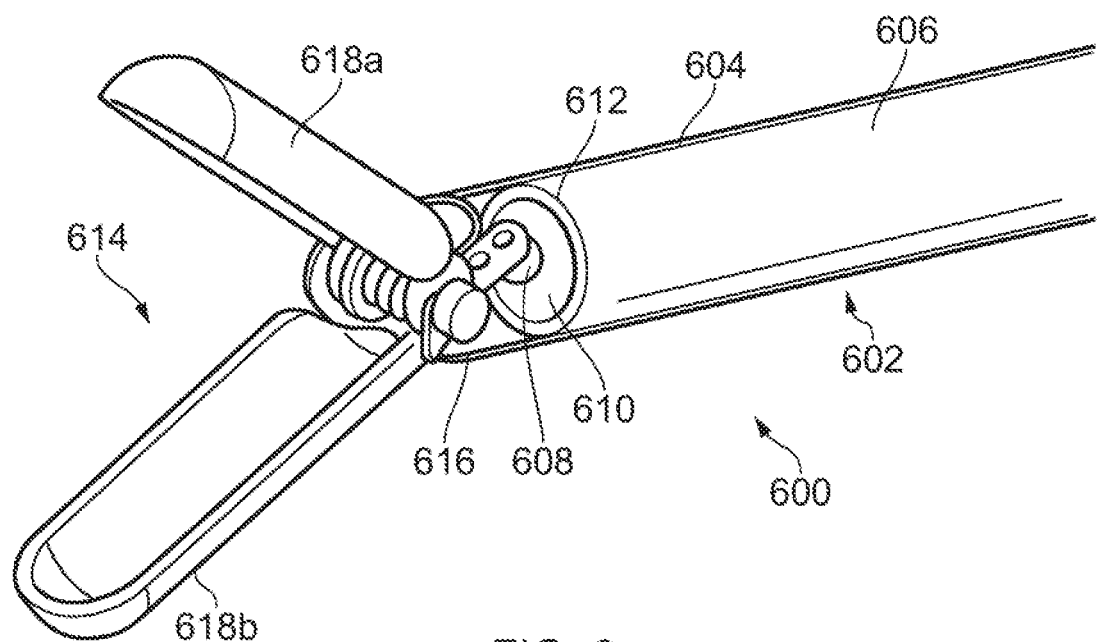
FIG. 6 is a schematic perspective view of the distal end of a biopsy forceps tool that is another embodiment of the invention.

FIG. 6 shows a schematic representation of an endoscopic biopsy forceps tool 600 according to another embodiment. The forceps tool 600 comprises a feed cable 602 that has an outer diameter sized to be suitable for passing through the instrument channel of an endoscope or similar scoping device. In this embodiment, the feed cable 602 comprises an outer sleeve 604 that encases a coaxial cable 606. The coaxial cable 606 and the portion of the sleeve that encases it may be flexible to enable the endoscope to manoeuvre the instrument into position.

The coaxial cable comprises an inner conductor 608 that is surrounded by a dielectric material 610, which in turn is surrounded by an outer conductor 612. The outer conductor 612 and dielectric material 610 terminate within the sleeve 604 to form a distal end of the coaxial cable. The inner conductor 608 protrudes beyond the distal end of the coaxial cable to connect with a distal jaw assembly 614 as discussed below.

A distal portion 616 of the sleeve 604 extends beyond the distal end of the coaxial cable and terminates at the distal jaw assembly 614. The distal portion 616 may be formed from a short rigid section in order to provide physical support for the distal jaw assembly.

The distal jaw assembly 614 comprises a pair of jaws 618a, 618b, each of which has a elongate trough or cup shape. The pair of jaws 618a, 618b are disposed opposite each other on the distal portion 616, and are movable relative to each other between a closed position in which they enclose an internal volume formed by their elongate troughs, and an open position in which they are angled apart to receive biological tissue. The distal jaw assembly is depicted in the open configuration in FIG. 6.

In this embodiment, the pair of jaws 618a, 618b are rotatable about a hinge that is formed from a lateral rod that extends across the opening of the distal portion 616 of the sleeve 604. Each of the pair of jaws 618a, 618b has a proximal mounting ring that is rotatably mounted on the lateral rod. The inner conductor 608 is connected to the lateral rod in order to feed microwave energy conveyed by the coaxial cable to the pair of jaws.

In this embodiment, the pair of jaws may be moved between the open and closed configurations by sliding an actuator sleeve (not shown) along the feed cable 602 beyond the distal portion 606 of the sleeve 604. To assist opening, the hinge may include a spring or the like to bias the pair of jaws into the open configuration.

Figure 7:
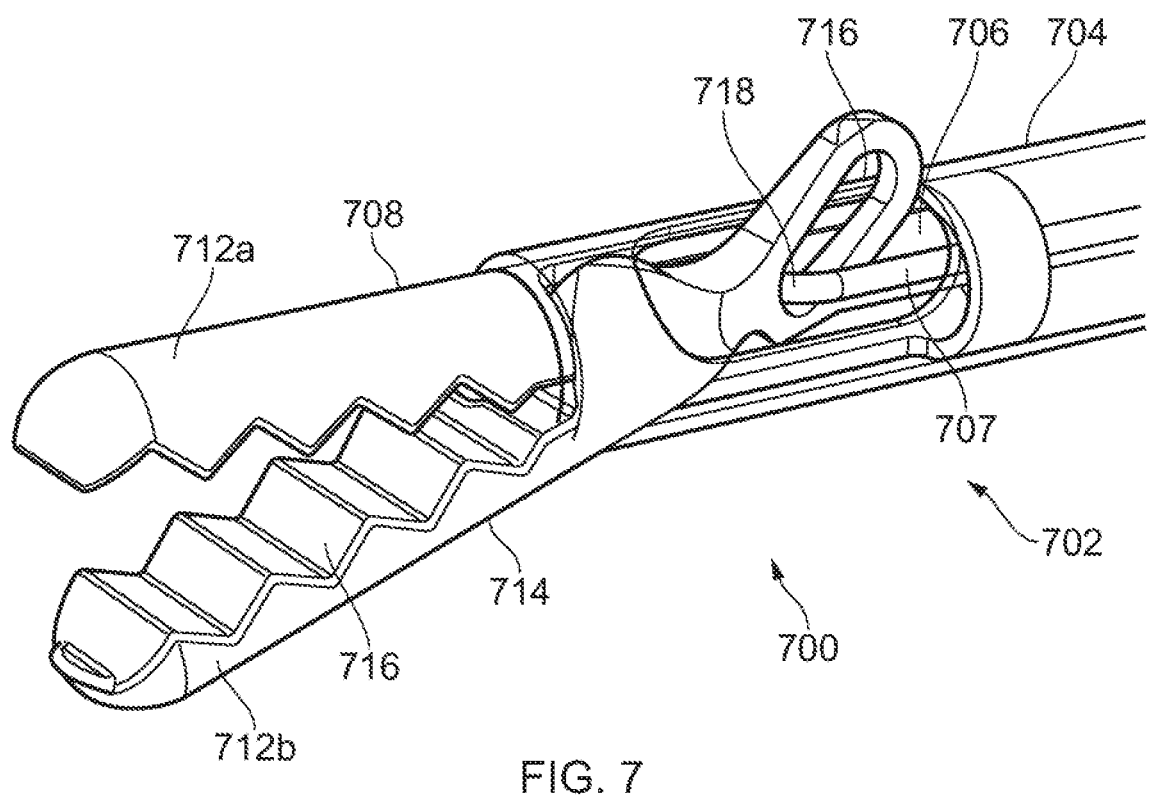
FIG. 7 is a schematic perspective view of the distal end of a biopsy forceps tool that is yet another embodiment of the invention.

FIG. 7 shows a schematic representation of an endoscopic biopsy forceps tool 700 according to another embodiment. The forceps tool 700 comprises a feed cable 702 that has an outer diameter sized to be suitable for passing through the instrument channel of an endoscope or similar scoping device. In this embodiment, the feed cable 702 comprises a hollow sleeve 704 that defines a lumen. A coaxial cable 706 and a control rod 707 extend through the lumen from a proximal end to a distal end thereof.

In this embodiment, a fixed jaw element 708 is secured at the distal end of the sleeve 704. The fixed jaw element 708 has a proximal portion that lies inside the sleeve 704 to provide a support frame for receiving distal ends of the coaxial cable 706 and control rod 707. The support frame may include a recess shaped to fit with the outer surface of the coaxial cable.

The fixed jaw element 708 has a distal portion that protrudes from the sleeve 704 to form one of a pair of jaws 712a, 712b, which provide a function similar to the pairs of jaws discussed above. In particular, the jaw 712a on the fixed jaw element may have an elongate trough shape, whereby it defines an internal volume for receiving biological tissue that is gripped between the pair of jaws. The fixed jaw element 708 may be constructed out of a conductive material (e.g. stainless steel 316L), thereby creating a return path between the jaw 712a and the outer conductor of the coaxial cable whilst also improving the strength to the tip of the product once fully assembled. The coaxial cable may be soldered to the fixed jaw element.

A movable jaw element 714 is mounted in the distal end of the sleeve 704. The movable jaw element is pivotably connected to the fixed jaw element 708 to rotate about a pivot axis that is fixed relative to the fixed jaw element and sleeve. The fixed jaw element 708 therefore acts as both a pivot for the movable jaw element and as a fixture point for the coaxial cable 706. The pivotal connection may be formed by a laterally protruding pivot bar on the movable jaw element, which is received in a cooperating hole on the fixed jaw element. The movable jaw element 714 has a proximal portion that includes an elongate slot 716 that engages with a lateral engagement finger 718 formed on the control rod. The elongate slot 716 acts as a cam to transform longitudinal motion of the control rod 707 relative to the sleeve into pivoting motion of the movable jaw element 712b relative to the fixed jaw element 712a. The control rod may be made from nitinol or the like. The movable jaw element 714 has a distal portion that protrudes from the sleeve 704 to form a jaw 712b forms a pair of jaws with the jaw 712a on the fixed jaw element. In this embodiment, the jaw 712b has a ridged (saw-tooth) surface 716 that faces the other jaw 712a. The movable jaw 712a is arranged to pivot between a closed position in which it abuts the bottom edge of the jaw 712a to enclosed the internal volume and an open position (shown in FIG. 7) in which there is a space between the jaws 712a, 712b to receive biological tissue.

The movable jaw element may be constructed primarily from non-conductive material, such as ceramic or PEEK. A conductive coating or layer or track (not shown) is formed on the ridged surface. The inner conductor of the coaxial cable is connected to the conductive coating so that microwave energy conveyed by the coaxial cable is delivered to the pair of jaws to assist in the coagulation of blood.

To provide space for operation of the cam mechanism discussed above, the sleeve 704 may have a opening 718 in a distal portion thereof. The distal opening of the sleeve may also be shaped to permit full opening of the pair of jaws.

The invention claimed is:

1. A biopsy forceps tool comprising:
   a coaxial cable for conveying microwave energy, the coaxial cable having an inner conductor, an outer conductor and a layer of dielectric material separating the inner conductor from the outer conductor; and
   a jaw assembly mounted at a distal end of the coaxial cable, the jaw assembly comprising a pair of jaws, each of the pair of jaws comprising an electrically conductive shell, the jaw assembly being operable to change a relative position of the pair of jaws between a closed position in which the electrically conductive shells engage each other to enclose an internal volume for holding a tissue sample and an open position in which the electrically conductive shells are separated to expose the internal volume in order to receive the tissue sample, wherein the electrically conductive shells form a Faraday cage around the internal volume when in the closed position, wherein the coaxial cable is connected to deliver microwave energy to the jaw assembly to be emitted as a microwave field, and wherein the Faraday cage is configured to shield the internal volume from the microwave energy supplied by the coaxial cable.

2. The biopsy forceps tool according to claim 1, wherein each of the pair of jaws has a thermal insulation layer separating the electrically conductive shells from the internal volume.

3. The biopsy forceps tool according to claim 1, wherein the electrically conductive shells engage each other along opposing peripheral edges when the pair of jaws are in the closed position.

4. The biopsy forceps tool according to claim 3, wherein the opposing peripheral edges have a serrated or saw-tooth profile.

5. The biopsy forceps tool according to claim 3, wherein the opposing peripheral edges overlap when the pair of jaws are in the closed position.

6. The biopsy forceps tool according to claim 1, wherein the pair of jaws are pivotably connected to each other.

7. The biopsy forceps tool according to claim 1, wherein the pair of jaws are pivotable about a hinge at proximal ends of the pair of jaws.

8. The biopsy forceps tool according to claim 1, wherein the pair of jaws are biased towards the open position.

9. The biopsy forceps tool according to claim 1, including a sleeve arranged to surround the pair of jaws when the pair of jaws are in the closed position.

10. The biopsy forceps tool according to claim 9, wherein the sleeve is axially slidable relative to the pair of jaws between a forward position in which the sleeve covers the pair of jaws and a retracted position in which the pair of jaws protrude outwardly from the sleeve.

11. The biopsy forceps tool according to claim 10, wherein when the sleeve is in the forward position the pair of jaws are constrained to occupy the closed position and when the sleeve is slid into the retracted position the pair of jaws are able to adopt the open position.

12. The biopsy forceps tool according to claim 9, wherein the pair of jaws is axially slidable relative to the sleeve between a retracted position in which the sleeve covers the pair of jaws and an extended position in which the pair of jaws protrude from the sleeve.

13. The biopsy forceps tool according to claim 12, wherein when the pair of jaws are in the retracted position the pair of jaws are constrained to occupy the closed position and when the pair of jaws is slid into the extended position the pair of jaws are able to adopt the open position.

14. The biopsy forceps tool according to claim 12, wherein the coaxial cable has a terminal connector, the terminal connector being arranged at a distal end of the coaxial cable, the terminal connector having an axially extending conductive pin electrically connected to the inner conductor of the coaxial cable, and wherein the jaw assembly including a conductive tube slidably engaged with the conductive pin, the conductive tube being electrically connected to the electrically conductive shells of the pair of jaws.

15. The biopsy forceps tool according to claim 14, wherein the pair of jaws are moved axially by axial movement of the conductive tube.

16. The biopsy forceps tool according to claim 14, having a control rod connected to the conductive tube and movable axially relative to the coaxial cable, whereby the conductive tube is slidable relative to the conductive pin by movement of the control rod relative to the coaxial cable.

17. The biopsy forceps tool according to claim 16, wherein the control rod extends alongside the coaxial cable.

18. The biopsy forceps tool according to claim 16, wherein the inner conductor of the coaxial cable is hollow, and wherein the control rod extends through the hollow inner conductor.

19. The biopsy forceps tool according to claim 9, wherein the sleeve comprises an inner dielectric layer and an outer conductive layer that is electrically connected to the outer conductor of the coaxial cable, and wherein the electrically conductive shells are electrically connected to the inner conductor of the coaxial cable.

20. The biopsy forceps tool according to claim 19, wherein the inner dielectric layer of the sleeve abuts and electrically insulates the outer conductive layer of the sleeve from the electrically conductive shells of the pair of jaws.

21. The biopsy forceps tool according to claim 6, having a control rod extending alongside the coaxial cable, wherein the control rod is movable to change the relative position of the pair of jaws.

22. The biopsy forceps tool according to claim 21, wherein the control rod is movable axially relative to the coaxial cable, and wherein the jaw assembly includes a cam mechanism in engagement with the control rod to transform axial movement of the control rod into pivoting relative movement between the pair of jaws.

23. The biopsy forceps tool according to claim 21, wherein the control rod is rotatable, and wherein the jaw assembly includes a rotary joint in engagement with the control rod to transform rotating movement of the control rod into pivoting relative movement between the pair of jaws.

24. The biopsy forceps tool according to claim 1, wherein the jaw assembly and coaxial cable are dimensioned to fit within an instrument channel of an endoscope, bronchoscope, or gastroscope.

25. The biopsy forceps tool according to claim 1, having a protective feed cable surrounding the coaxial cable and jaw assembly.

26. The biopsy forceps tool according to claim 1, having a temperature sensor mounted in the internal volume.

27. The biopsy forceps tool according to claim 1, having a temperature sensor mounted on an outer surface of the jaw assembly.

* * * * *